US011647915B2

(12) United States Patent
Fielden et al.

(10) Patent No.: US 11,647,915 B2
(45) Date of Patent: May 16, 2023

(54) SYSTEMS AND METHODS FOR MEDICAL IMAGING INCORPORATING PRIOR KNOWLEDGE

(71) Applicant: University of Virginia Patent Foundation, Charlottesville, VA (US)

(72) Inventors: Samuel Fielden, Charlottesville, VA (US); Li Zhao, Charlottesville, VA (US); Max Wintermark, Charlottesville, VA (US); Craig H. Meyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1718 days.

(21) Appl. No.: 14/677,891

(22) Filed: Apr. 2, 2015

(65) Prior Publication Data

US 2015/0282719 A1 Oct. 8, 2015

Related U.S. Application Data

(60) Provisional application No. 61/974,217, filed on Apr. 2, 2014.

(51) Int. Cl.
*A61B 5/026* (2006.01)
*A61B 5/055* (2006.01)
*A61B 5/00* (2006.01)
*A61B 6/00* (2006.01)

(52) U.S. Cl.
CPC .......... *A61B 5/0263* (2013.01); *A61B 5/0042* (2013.01); *A61B 5/055* (2013.01); *A61B 6/5229* (2013.01); *A61B 2576/026* (2013.01)

(58) Field of Classification Search
CPC ..... A61B 5/0263; A61B 5/055; A61B 5/0042; A61B 2576/026
See application file for complete search history.

(56) References Cited

U.S. PATENT DOCUMENTS

| 9,183,626 B2* | 11/2015 | Zhao ............... G06T 11/005 |
| 2010/0204563 A1* | 8/2010 | Stodilka ............. G01R 33/481 600/411 |
| 2012/0195485 A1* | 8/2012 | Matsuba ............. A61B 5/0263 382/131 |
| 2013/0278261 A1* | 10/2013 | Fielden ............. G01R 33/5608 324/309 |
| 2014/0062477 A1* | 3/2014 | Carroll ............. G01R 33/4826 324/309 |

OTHER PUBLICATIONS

Rousseau et al.; A non-local approach for image super-resolution using intermodality priors; published on May 6, 2010; Medical Image Analysis; vol. 14, Issue 4; p. 594-605 (Year: 2010).*

(Continued)

*Primary Examiner* — Chao Sheng
(74) *Attorney, Agent, or Firm* — Meunier Carlin & Curfman LLC (57) ABSTRACT

Aspects of the present disclosure relate to systems and methods for medical imaging that incorporate prior knowledge. Some aspects relate to incorporating prior knowledge using a non-local means filter. Some aspects relate to incorporating prior knowledge for improved perfusion imaging, such as those incorporating arterial spin labeling.

19 Claims, 5 Drawing Sheets

(56) References Cited

OTHER PUBLICATIONS

Van Gelderen et al.; Pittfalls of MRI measurement of white matter perfusion based on arterial spin labeling; published on Mar. 27, 2008; Magnetic Resonance in Medicine; vol. 59, Issue 4; pp. 788-795 (Year: 2008).*
Wikipedia; k-space (magnetic resonance imaging); https://en.wikipedia.org/wiki/K-space_(magnetic_resonance_imaging) (Year: 2022).*
Hansen et al.; Image reconstruction: an overview for clinicians.; published online on Jun. 25, 2014; Journal of magnetic resonance imaging : JMRI, 41(3), 573-585. https://doi.org/10.1002/jmri.24687 (Year: 2014).*
Buades, A. et al., "A Review of Image Denoising Algorithms, With a New One," SIAM Journal on Multiscale Modeling and Simulation: A SIAM Interdisciplinary Journal, 2005, pp. 490-530, 4(2).
Dai, W. et al., "Continuous Flow Driven Inversion for Arterial Spin Labeling Using Pulsed Radiofrequency and Gradient Fields," Magn Reson Med., 2008, pp. 1448-1497, 60(6), Wiley-Liss, Inc.
Detre, J.A. et al., "Perfusion Imaging," Magn Reson Med., 1992, pp. 37-45, 23(1).
Kim, T. et al., "Whole brain perfusion measurements using arterial spin labeling with multiband acquisition," Magn Reson Med. 2013, pp. 1653-1661, 70(6), Wiley Periodicals, Inc.
Robson, P.M. et al., "Strategies for Reducing Respiratory Motion Artifacts in Renal Perfusion Imaging with Arterial Spin Labeling," Magn Reson Med., 2008, pp. 1374-1387, 61(6).

* cited by examiner

SYSTEMS AND METHODS FOR MEDICAL IMAGING INCORPORATING PRIOR KNOWLEDGE

CROSS REFERENCE TO RELATED APPLICATIONS

This application claims benefit, under 35 U.S.C. §119(e), to U.S. Provisional Application No. 61/974,217 filed Apr. 2, 2015, entitled "Introducing Prior Knowledge Through the Non-Local Means Filter in Model-Based Reconstructions Improves ASL Perfusion Imaging." The entire contents and substance of that application is hereby incorporated by reference herein as if fully set forth below.

STATEMENT OF FEDERALLY SPONSORED RESEARCH

This invention was made with government support under NIH R01 HL079110 and NIH T32 HL007284, awarded by the National Institutes of Health. The government has certain rights in the invention.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference. In terms of notation, hereinafter, "[n]" may represent the nth reference cited in the reference list. For example, [5] represents the 5th reference cited in the reference list, namely, Tae Kim, Zhao, et al., Whole brain perfusion measurements using arterial spin labeling with multiband acquisition, 70 MAGNETIC RESONANCE IN MEDICINE 1653-1661 (2013).

BACKGROUND

Arterial Spin Labeling (ASL) permits the noninvasive measurement of perfusion with Magnetic Resonance Imaging (MRI). Rather than injecting a flow tracer, ASL can employ radio frequency and magnetic field gradient pulses to invert naturally existing water spins in the feeding arteries. The technique shows promise for clinical evaluation of central nervous system disorders and is a useful investigational tool. Labeling of arterial blood can be achieved with a number of different strategies. Continuous ASL attempts to continuously invert or saturate blood as it passes a particular plane. Pulsed ASL employs a single pulse to define a volume containing arterial blood for labeling [1].

A significant challenge for ASL is low Signal-to-Noise Ratio (SNR) and low spatial resolution of the resulting images, since ASL is a subtractive technique, with the perfusion signal typically amounting to less than 2% of the component signal. Among other advantages, the SNR and spatial resolution of perfusion images acquired with ASL can be improved by incorporating side information from high-SNR anatomical images into model-based reconstructions of the data, as is accomplished by some embodiments of this disclosure.

It is with respect to these and other considerations that the various embodiments described below are presented.

SUMMARY

The present disclosure relates medical imaging using incorporation of prior knowledge. In some embodiments, the prior knowledge includes a high-resolution image used as part of the cost function used to reconstruct a lower-resolution image. In some embodiments, the medical images are generated by magnetic resonance imaging, although other types of medical images are contemplated. In some embodiments, the system includes a non-local means filter, which filters pixels in an image based on pixels outside of the immediate neighborhood of the processed pixel.

In one aspect, the present disclosure relates to a method that includes: acquiring perfusion image data corresponding to an area of interest of a subject; acquiring anatomical image data corresponding to the area of interest of the subject; determining, based on the anatomical image, filter weights for a cost function to apply to the perfusion image data; and applying the cost function, comprising the determined filter weights, to the perfusion image data to generate enhanced image data associated with at least one physiological activity of the subject in the area of interest.

In some embodiments, the perfusion image data is acquired by magnetic resonance imaging. In some embodiments, the perfusion image data corresponds to magnetic resonance imaging functions that include arterial spin labeling (ASL). In some embodiments, the cost function incorporates anatomical boundary information in a regularization term. In some embodiments, the enhanced image data has a higher signal-to-noise ratio than an image generated from the perfusion image data by an inverse Fourier transform. In some embodiments, the cost function includes a non-local means filter. In some embodiments, the cost function includes a differencing matrix. In some embodiments, the perfusion image data has a lower signal-to-noise ratio than the anatomical image data. In some embodiments, the anatomical image data is acquired concurrently with the acquisition of the perfusion image data. In some embodiments, the area of interest includes at least one area of the brain of the subject and the at least one physiological activity includes cerebral blood flow (CBF) in the brain of the subject.

In another aspect, the present disclosure relates to a system. In an embodiment, the system includes at least one image data acquisition device configured to: obtain perfusion image data corresponding to an area of interest of a subject and obtain anatomical image data corresponding to the area of interest of the subject. The system also includes an image processing device coupled to the at least one image data acquisition device and configured to: receive the first perfusion image data; receive the anatomical image data; determine, based on the anatomical image, filter weights for a cost function to apply to the perfusion image data; and apply the cost function, comprising the determined filter weights, to the perfusion image data to generate enhanced image data associated with at least one physiological activity of the subject in the area of interest.

In some embodiments, the perfusion image data is acquired by magnetic resonance imaging. In some embodiments, the perfusion image data corresponds to magnetic resonance imaging functions that include arterial spin labeling (ASL). In some embodiments, the cost function incorporates anatomical boundary information in a regularization term. In some embodiments, the enhanced image data has a higher signal-to-noise ratio than an image generated from the perfusion image data by an inverse Fourier transform. In some embodiments, the cost function includes a non-local means filter. In some embodiments, the cost function includes a differencing matrix. In some embodiments, the perfusion image data has a lower signal-to-noise ratio than the anatomical image data. In some embodiments, the anatomical image data is acquired concurrently with the acquisition of the perfusion image data. In some embodiments, the area of interest includes at least one area of the brain of the subject and the at least one physiological activity includes cerebral blood flow (CBF) in the brain of the subject.

In yet another aspect, the present disclosure relates to a computer-readable medium. In an embodiment, the computer-readable medium stores instructions that, when executed by one or more processors, cause a computer to: acquire perfusion image data corresponding to an area of interest of a subject; acquire anatomical image data corresponding to the area of interest of the subject; determine, based on the anatomical image, filter weights for a cost function to apply to the perfusion image data; and apply the cost function, comprising the determined filter weights, to the perfusion image data to generate enhanced image data associated with at least one physiological activity of the subject in the area of interest.

In some embodiments, the perfusion image data is acquired by magnetic resonance imaging. In some embodiments, the perfusion image data corresponds to magnetic resonance imaging functions that include arterial spin labeling (ASL). In some embodiments, the cost function incorporates anatomical boundary information in a regularization term. In some embodiments, the enhanced image data has a higher signal-to-noise ratio than an image generated from the perfusion image data by an inverse Fourier transform. In some embodiments, the cost function includes a non-local means filter. In some embodiments, the cost function includes a differencing matrix. In some embodiments, the perfusion image data has a lower signal-to-noise ratio than the anatomical image data. In some embodiments, the anatomical image data is acquired concurrently with the acquisition of the perfusion image data. In some embodiments, the area of interest includes at least one area of the brain of the subject and the at least one physiological activity includes cerebral blood flow (CBF) in the brain of the subject.

Other aspects and features according to the present disclosure will become apparent to those of ordinary skill in the art, upon reviewing the following detailed description in conjunction with the accompanying figures.

BRIEF DESCRIPTION OF THE FIGURES

Reference will now be made to the accompanying drawings, which are not necessarily drawn to scale.

DETAILED DESCRIPTION

Aspects of the present disclosure relate to medical imaging that incorporates prior knowledge. Among other benefits and advantages, practicing aspects of the present disclosure in accordance with one or more example embodiments described herein provides for improved signal-to-noise ratios, mean percent error, and peak SNR for short duration medical images, such as those used in MRI perfusion imaging. These benefits can also be achieved for ASL perfusion imaging.

Although example embodiments of the present disclosure are explained in detail, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Further, it is contemplated that one or more data acquisition or data collection steps of a method may include acquiring, collecting, receiving, or otherwise obtaining data.

By way of example, data acquisition or collection may include acquiring data via a data acquisition device, receiving data from an on-site or off-site data acquisition device or from another data collection, storage, or processing device. Similarly, data acquisition or data collection devices of a system may include any device configured to acquire, collect, or otherwise obtain data, or to receive data from a data acquisition device within the system, an independent data acquisition device located on-site or off-site, or another data collection, storage, or processing device.

As discussed herein, a "subject" or "patient" may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g. rat, dog, pig, monkey), etc. It should be appreciated that the subject may be any applicable human patient, for example.

As discussed herein, a "non-local means filter" can be a filter that takes a mean of a plurality of pixels in the image, weighted by how similar each pixel is to the input pixel to generate an output pixel. Where $\Omega$ is the area of an image, and p and q are two points within the image, an example non-local means filter is given by the expression:

$$u(p) = \frac{1}{C(p)} \int_\Omega v(q) f(p, q) \, dq$$

where u(p) is the filtered value of the image at point p, v(q) is the unfiltered value of the image at point q, $f(p,q)$ is the weighting function, and the integral is evaluated for all values q in $\Omega$. C(p) is a normalizing factor, given by:

$$C(p) = \int_\Omega f(p,q) \, dq$$

The normalizing function $f(p,q)$ is used to determine how closely related the image at point p is to the image at point q. As is appreciated by persons of ordinary skill in the art, numerous weighting functions can be used, as can other variants of non-local means filtering. In summary, non-local means filter encompasses all filtering methods that calculate the value of a resulting pixel based on information collected outside of the neighborhood of the resulting pixel.

Figure 1:
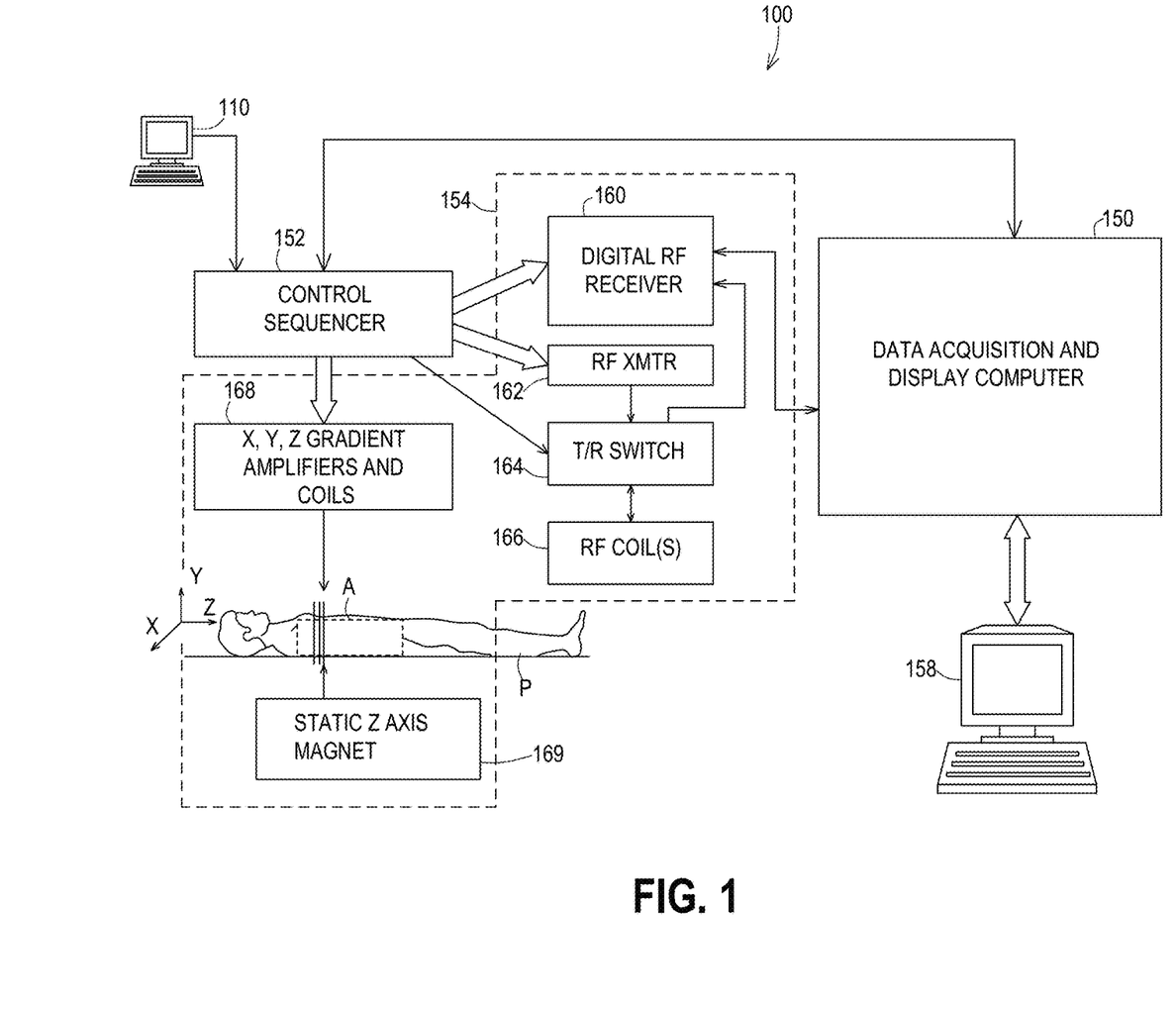
FIG. 1 is a system diagram illustrating an operating environment capable of implementing aspects of the present disclosure.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest A corresponds to a region associated with one or more physiological activities in patient P. The area of interest shown in the example embodiment of FIG. 1 corresponds to a chest region of patient P, but the area of interest for purposes of implementing aspects of the disclosure presented herein is not limited to the chest area. It should be recognized and appreciated that the area of interest can be one or more of a brain region, heart region, and upper or lower limb regions of the patient P, for example. Physiological activities that may be analyzed by methods and systems in accordance with various embodiments of the present disclosure may include, but are not limited to, muscular movement or fluid flow in particular areas of interest.

It should be appreciated that any number and type of computer-based medical imaging systems or components, including various types of commercially available medical imaging systems and components, may be used to practice aspects of the present disclosure. The scope of the disclosure is not specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
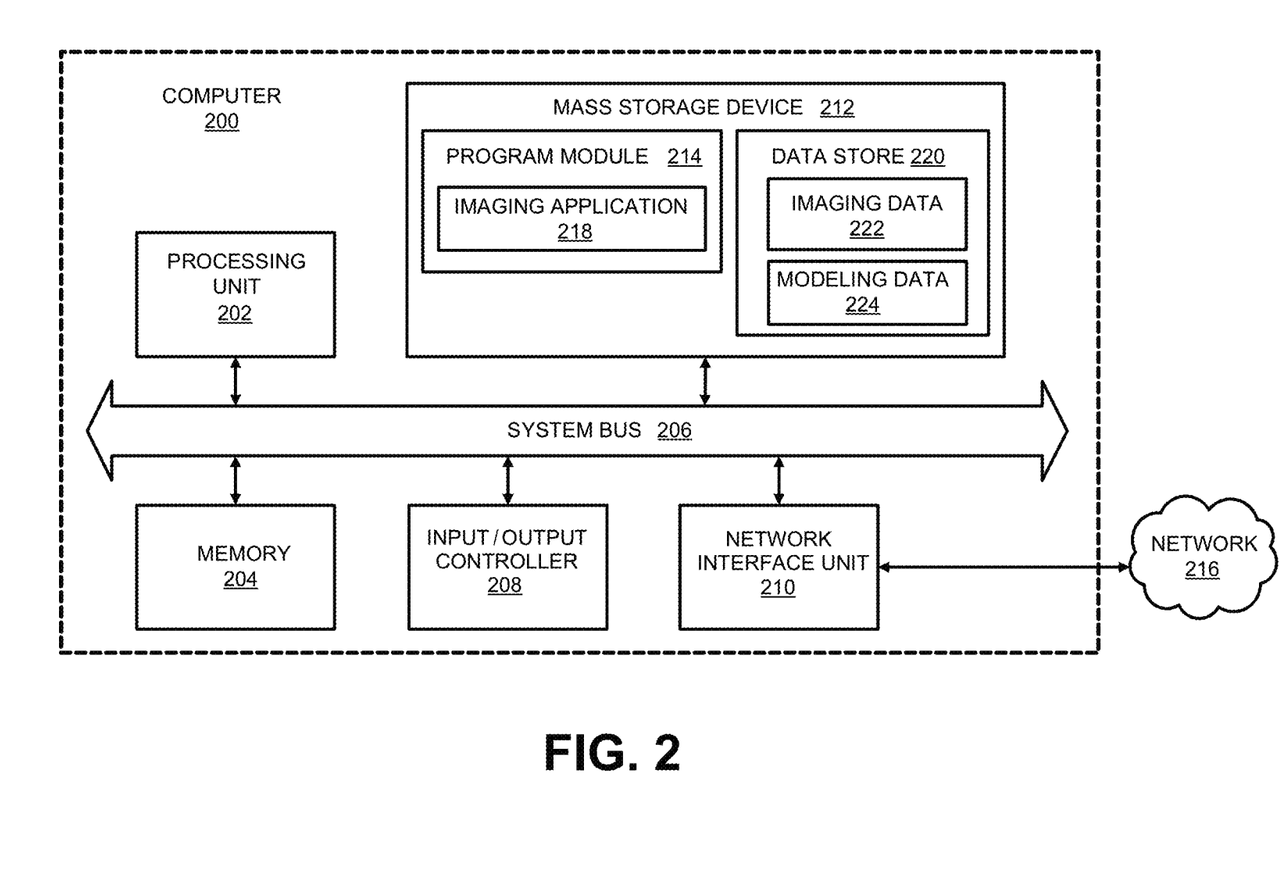
FIG. 2 is a computer architecture diagram showing a general computing system capable of implementing aspects of the present disclosure.

FIG. 2 is a computer architecture diagram showing a general computing system capable of implementing aspects of the present disclosure in accordance with one or more example embodiments described herein. A computer 200 may be configured to perform one or more functions associated with embodiments illustrated in one or more of FIGS. 3A-D and FIGS. 4A-C. For example, a computer 200 can be configured to perform a reconstruction process of imaging data, such as k-space data, where the reconstruction incorporates prior knowledge. It should be appreciated that the computer 200 may be implemented within a single computing device or a computing system formed with multiple connected computing devices. The computer 200 may be configured to perform various distributed computing tasks, which may distribute processing and/or storage resources among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform one or more functions associated with embodiments illustrated in one or more of FIGS. 3A-D, and FIGS. 4A-C discussed below. The program modules 214 may include an imaging application 218 for processing images in accordance with one or more embodiments described herein. The computer 200 can include a data store 220 for storing data that may include imaging-related data 222 such as image acquisition data, and a modeling data store 224 for storing image modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. Transitory signals are not "computer-storage media", "computer-readable storage medium", or "computer-readable storage media" as described herein.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 200 may also include an input/output controller 208 for receiving and processing input from a number of input devices. Input devices may include one or more of keyboards, mice, stylus, touchscreens, microphones, audio capturing devices, or image/video capturing devices. An end user may utilize such input devices to interact with a user interface, for example a graphical user interface, for managing various functions performed by the computer 200.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state, or may include rotating media storing magnetically-encoded information. The program modules 214, which include the imaging application 218, may include software instructions that, when loaded into the processing unit 202 and executed, cause the computer 200 to provide functions associated with embodiments illustrated in FIGS. 3A-D and FIGS. 4A-C. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

The incorporation of prior knowledge regarding image features can improve image quality for many imaging methodologies, including in perfusion imaging with ASL [2]. In some embodiments, prior information regarding the perfusion distribution exists. In some embodiments, it can be restricted to white and gray matter, and thus not distributed uniformly across known anatomical boundaries. In these embodiments, the imposition of side information from high resolution, high SNR anatomical images has the potential to improve perfusion imaging. In some embodiments, a non-local means denoising algorithm can be applied to perfusion image data. In some embodiments, a denoising algorithm can use spatial information derived from concurrently-acquired anatomical images to build the filter weights.

Anatomic side information can be incorporated into perfusion reconstructions by introducing boundary information into the regularization term in a cost function used to estimate the image in iterative model-based reconstructions. For example, in an embodiment using a non-local means filter, the cost function can comprise:

$$\hat{f} = \underset{f}{\operatorname{argmin}} \|y - Af\|_2 + \beta_{NLM}\|f - NLM(f, p)\|_1 + \beta_{TV}\|Cf\|_1$$

Where C is a differencing matrix used to apply a small total variation penalty and NLM(f,p) is a non-local means filtered version of the image, trained on an anatomical image p. In some embodiments, the cost function may incorporate an unfiltered anatomical image p. In some embodiments, the differencing matrix may be omitted.

A non-local means filter works on the principle that any local image patch should look similar to other image patches present in the same image [3]. In some embodiments, the filter can be deployed on a high-SNR, high spatial anatomical image p, as the low-SNR perfusion data may not contain much spatial information. In some embodiments, the calculated filter weights can be saved and can be used to guide the perfusion filter by describing, for any individual patch, which other patches in the (perfusion) image, f, should be similar and how to combine them.

Figure 5:
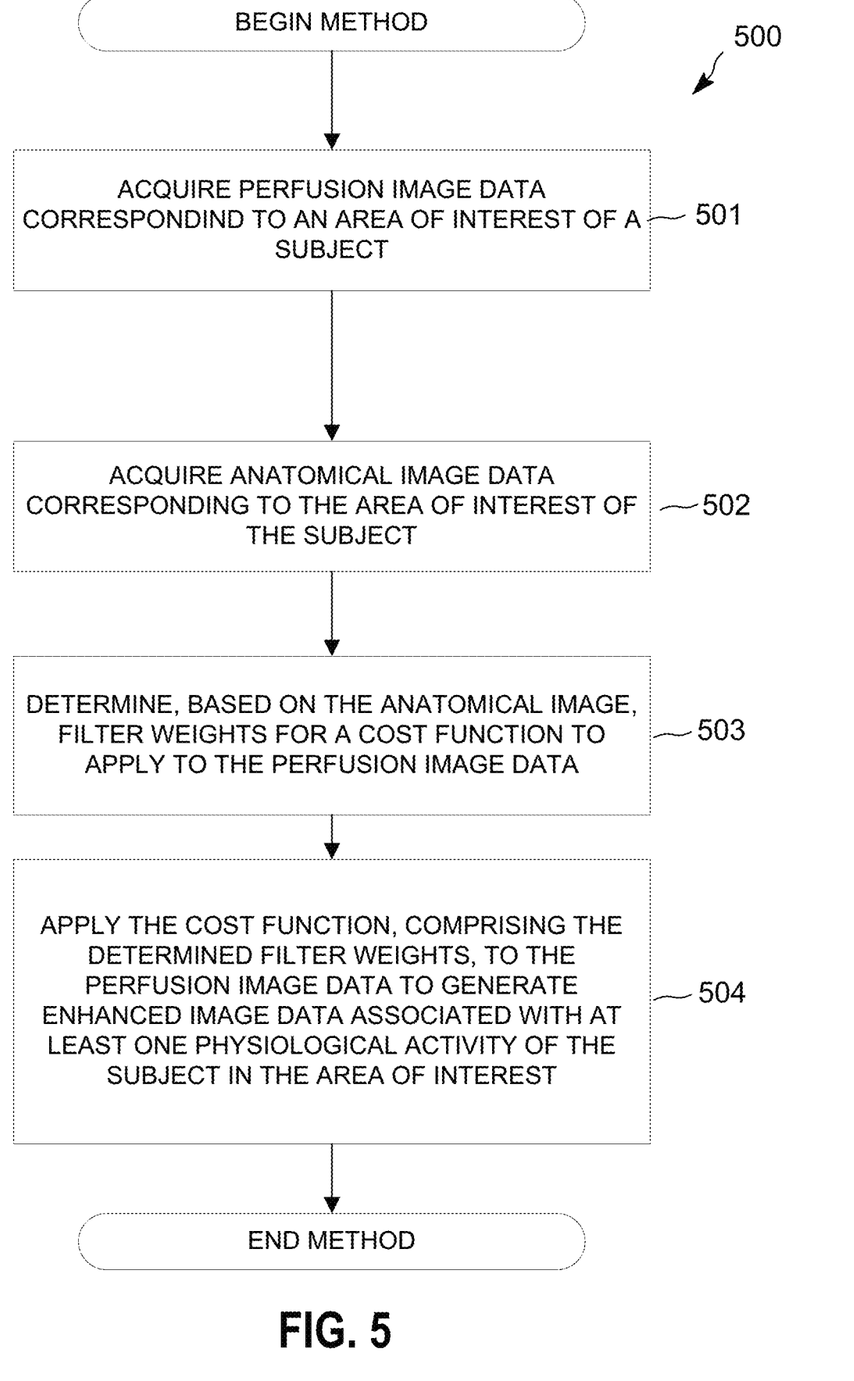
FIG. 5 is a flow diagram illustrating operations of a method for reconstructing a perfusion image of an area of interest of a subject, according to one embodiment of the present disclosure.

FIG. 5 is a flow diagram illustrating operations of a method 500 for accelerated imaging of an area of interest of a subject, according to one embodiment of the present disclosure. As shown, the method 500 includes operation 501, where perfusion image data is acquired corresponding to an area of interest of a subject. The method 500 further includes operation 502, wherein anatomical image data is acquired corresponding to the area of interest of the subject. In some embodiments, the anatomical image data has a higher resolution than the perfusion image data. The method 500 further includes determining, based on the anatomical image, filter weights for a cost function to apply to the perfusion image data. The method 500 further includes operation 504, where the cost function, comprising the determined filter weights, is applied to the perfusion image data to generate enhanced image data associated with at least one physiological activity of the subject in the area of interest. Operation 504 can be a reconstruction of k-space data from, for example, an MRI system, which is reconstructed into an image.

The acquiring perfusion image data may be acquired by magnetic resonance imaging. The perfusion image data can correspond to magnetic resonance imaging functions that comprise arterial spin labeling (ASL). The cost function can incorporate anatomical boundary information in a regularization term. The enhanced image data can have a higher signal-to-noise ratio than an image generated from the perfusion image data by an inverse Fourier transform.

The cost function can comprise a non-local means filter. The cost function can comprise a differencing matrix. The perfusion image data can have a lower signal-to-noise ratio than the anatomical image data. The anatomical image data can be acquired concurrently with the acquisition of the perfusion image data. The area of interest can comprise at least one area of the brain of the subject and the at least one physiological activity can comprise cerebral blood flow (CBF) in the brain of the subject.

Example Implementations and Results

The following describes examples of implementing some aspects of the present disclosure, and corresponding results.

Simulations

Figure 3A:
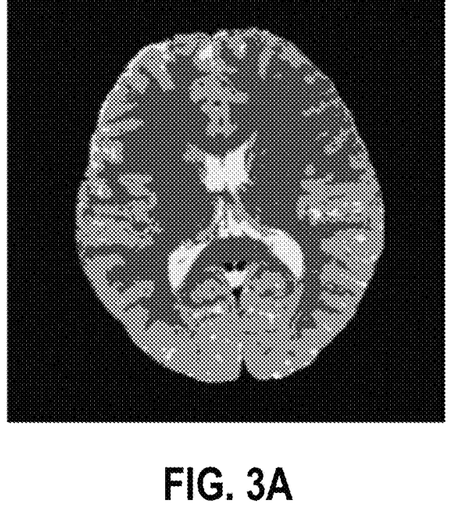
FIG. 3A is an anatomical image used to train a non-local means filter of an area of interest of a patient.
Figure 3B:
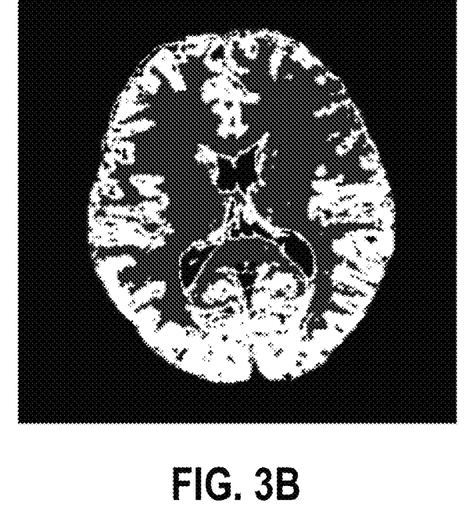
FIG. 3B is an ideal high-SNR, high-resolution perfusion image of the area of interest shown in FIG. 3A.

To test an embodiment of the present invention, a simulated experiment was performed. A T2-weighted brain image was segmented into white matter, gray matter, CSF, and background (FIG. 3A). To this segmented image, a small complex noise was added to create an "ideal", high-SNR anatomical reference image (FIG. 3B). Next, the CSF was removed, the white matter intensity reduced, the data truncated in k-space, and more noise was added in order to generate a simulated noisy, low-resolution perfusion data set. The resulting k-space data was then reconstructed with a standard inverse Fourier transform (iFFT—FIG. 3C) as well as a model-based reconstruction in which side information was imposed through the method described above (FIG. 3D). Using the "ideal" high-SNR perfusion image as the reference, the SNR, mean percent error (MPE), and peak SNR (PSNR: a measure of image similarity between each reconstruction and the reference perfusion image) was recorded for the iFFT and constrained reconstructions. In a numerical phantom derived from a T2-weighted anatomical image, the application of model-based iterative reconstructions improves SNR, resolution, and reduces error (FIG. 3D, Table 1). Compared to the standard inverse Fourier transform reconstruction, the model-based reconstruction improves SNR in white matter by 7% and in gray matter by 225%, decreases MPE of white and gray matter image intensities, and increases PSNR by improving resolution.

In-Vivo Experiments

Figure 4A:
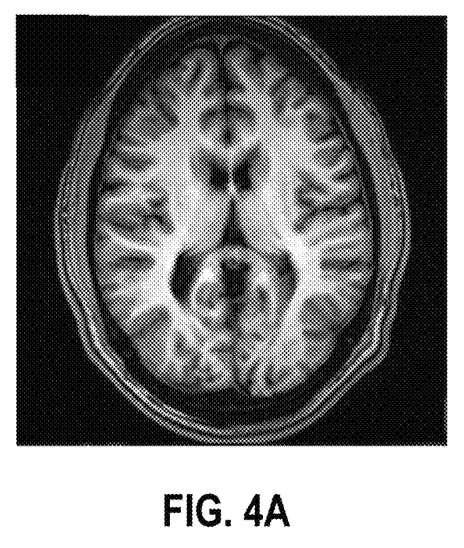
FIG. 4A is a T1-weighted image of an area of interest of a patient used to constrain model-based reconstructions
Figure 4B:
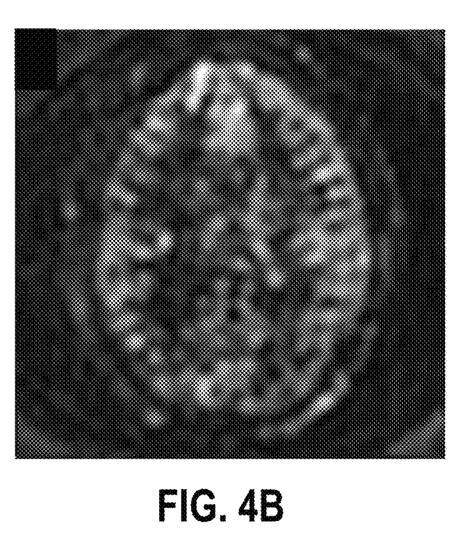
FIG. 4B is an iFFT reconstruction of a perfusion image of the area of interest shown in FIG. 4A.
Figure 4C:
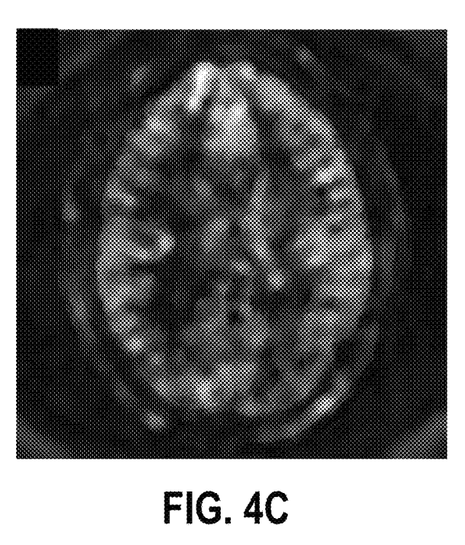
FIG. 4C is a constrained reconstruction regularized towards a side-information-trained NLM denoised image of the area of interest shown in FIG. 4A.

An in vivo experiment was carried out on 3T Trio Siemens scanner with a 12-channel head coil. FIG. 4A illustrates a T1-weighted 3D MP-RAGE (TR/TE=1900/3.5 ms) image with isotropic 0.8 mm$^3$ resolution provided high contrast between gray and white matter in order to supply high-quality boundary information. Three-D pseudo continuous ASL [4] was performed with a bolus duration=2000 ms, post label delay=1000 ms, and BIR4 adiabatic pulses to achieve intravascular flow suppression. Images were acquired with a 3D TSE stack-of-spirals sequence with 3 interleaves per slice [5]. Each interleaf had a readout duration of 6 ms and 24 slices were collected for an overall resolution 4×4×5 mm3. TR/TE were 5000 ms/22 ms. As before, the standard iFFT reconstruction was performed (shown in FIG. 4B) as well as a constrained reconstruction with a bias towards a side-information trained non-local-means filtered version of the image (shown in FIG. 4C). In vivo, the model-based reconstruction shown in FIG. 4C improves image SNR over the iFFT reconstruction in white matter by 12% and in gray matter by 32%.

TABLE 1

Figure 3C:
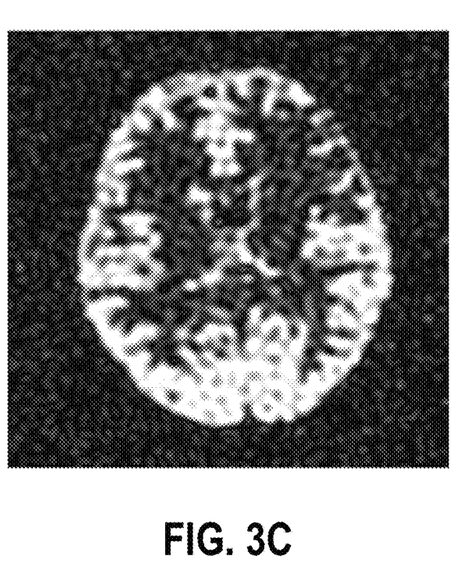
FIG. 3C is an iFFT reconstruction of low resolution, noisy data image of the area of interest shown in FIG. 3A.
Figure 3D:
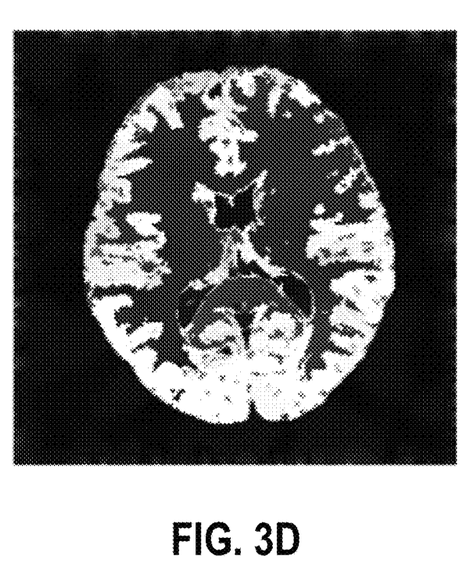
FIG. 3D is a constrained reconstruction of low resolution, noisy data image of the area of interest shown in FIG. 3A.

Quantification of Reconstruction Performance from FIG. 3A-C

| | iFFT Reconstruction | | | Constrained Reconstruction | | |
|---|---|---|---|---|---|---|
| | SNR | MPE | PSNR | SNR | MPE | PSNR |
| White Matter | 1.48 | 12.8% | 34.4 | 1.59 | 4.68% | 45.6 |
| Gray Matter | 3.83 | −16.5% | | 8.61 | −7.25% | |

CONCLUSION

The presently disclosed embodiments, therefore, are considered in all respects to be illustrative and not restrictive. The scope of the present disclosure is indicated by the appended claims, rather than the foregoing description, and all changes that come within the meaning and range of equivalents thereof are intended to be embraced therein.

REFERENCES

[1] John A. Detre et al., *Perfusion Imaging*, 23 MAGNETIC RESONANCE IN MEDICINE 37-45 (1992).
[2] Philip M. Robson et al. Strategies for reducing respiratory motion artifacts in renal perfusion imaging with arterial spin labeling, 61 MAGNETIC RESONANCE IN MEDICINE 1374-1387 (2009).
[3] Buades, et al., *A review of image denoising algorithms, with a new one*, 4 SIAM JOURNAL ON MULTISCALE MODELING AND SIMULATION 490-530 (2004).
[4] Weiying Dai, et al., Continuous Flow Driven Inversion for Arterial Spin Labeling Using Pulsed Radiofrequency and Gradient Fields, 60 MAGNETIC RESONANCE IN MEDICINE 1448-1497 (2008).
[5] Tae Kim, Zhao, et al., Whole brain perfusion measurements using arterial spin labeling with multiband acquisition, 70 MAGNETIC RESONANCE IN MEDICINE 1653-1661 (2013).

What is claimed is:

1. A method comprising:
acquiring raw complex-valued perfusion image data directly from a magnetic resonance imaging (MRI) scanner in a first scan covering an area of interest of a subject, wherein the acquisition uses arterial spin labeling (ASL) in k-space;
acquiring anatomical image data corresponding to the area of interest, by a second scan different from the first scan; and
applying a cost function to the raw complex-valued perfusion image data acquired directly from the MRI scanner, as part of an iterative reconstruction to form one or more enhanced perfusion images, wherein the cost function comprises a non-local means (NLM) filter trained with filter weights based on the anatomical image data.

2. The method of claim 1, wherein the one or more enhanced perfusion images has a higher signal-to-noise ratio than an image generated from the raw complex-valued perfusion image data by an inverse Fourier transform.

3. The method of claim 1, wherein the cost function comprises a differencing matrix.

4. The method of claim 1, wherein the raw complex-valued perfusion image data has a lower signal-to-noise ratio than the anatomical image data.

5. The method of claim 1, wherein the anatomical image data is acquired concurrently with the acquisition of the raw complex-valued perfusion image data.

6. The method of claim 1, wherein the area of interest comprises at least one area of the brain of the subject and the at least one physiological activity comprises cerebral blood flow (CBF) in the brain of the subject.

7. The method of claim 1, further comprising training, from the anatomical image data, a model to produce the trained model.

8. A system comprising
a magnetic resonance imaging (MRI) device;
a memory device;
at least one processor coupled to the memory device and the MRI device and storing computer-readable instructions which, when executed by the at least one processor, cause the system to perform functions that include:
acquiring raw complex-valued perfusion image data directly from the magnetic resonance image device scanner in a first scan covering an area of interest of a subject, wherein the acquisition uses arterial spin labeling (ASL) in k-space;
acquiring anatomical image data corresponding to the area of interest, by a second scan different from the first scan; and
acquiring a cost function to the raw complex-valued perfusion image data acquired directly from the MRI scanner, as part of an iterative reconstruction to form one or more enhanced perfusion images, wherein the cost function comprises a non-local means (NLM) filter trained with filter weights based on the anatomical image data.

9. The system of claim 8, wherein the one or more enhanced perfusion images has a higher signal-to-noise ratio than an image generated from the raw complex-valued perfusion image data by an inverse Fourier transform.

10. The system of claim 8, wherein the cost function comprises a differencing matrix.

11. The system of claim 8, wherein the raw complex-valued perfusion image data has a lower signal-to-noise ratio than the anatomical image data.

12. The system of claim 8, wherein the anatomical image data is acquired concurrently with the acquisition of the raw complex-valued perfusion image data.

13. The system of claim 8, wherein the area of interest comprises at least one area of the brain of the subject and the at least one physiological activity comprises cerebral blood flow (CBF) in the brain of the subject.

14. A computer-readable medium storing instructions that, when executed by one or more processors, cause a computer to perform functions that comprise:
acquiring raw complex-valued perfusion image data directly from a magnetic resonance imaging (MRI) scanner in a first scan covering an area of interest of a subject, wherein the acquisition uses arterial spin labeling (ASL) in k-space;
acquiring anatomical image data corresponding to the area of interest, by a second scan different from the first scan; and
applying a cost function to the raw complex-valued perfusion image data acquired directly from the MRI scanner, as part of an iterative reconstruction to form one or more enhanced perfusion images, wherein the cost function comprises a non-local means (NLM) filter trained with filter weights based on the anatomical image data.

15. The computer readable medium of claim 14, wherein the one or more enhanced perfusion images has a higher signal-to-noise ratio than an image generated from the raw complex-valued perfusion image data by an inverse Fourier transform.

16. The computer readable medium of claim 14, wherein the cost function comprises a differencing matrix.

17. The computer readable medium of claim 14, wherein the raw complex-valued perfusion image data has a lower signal-to-noise ratio than the anatomical image data.

18. The computer readable medium of claim 14, wherein the anatomical image data is acquired concurrently with the acquisition of the raw complex-valued perfusion image data.

19. The computer readable medium of claim 14, wherein the area of interest comprises at least one area of the brain of the subject and the at least one physiological activity comprises cerebral blood flow (CBF) in the brain of the subject.

* * * * *